US012630883B2

(12) United States Patent
Takeuchi et al.

(10) Patent No.: US 12,630,883 B2
(45) Date of Patent: May 19, 2026

(54) TEST METHOD OF DIVIDING BLASTIC PLASMACYTOID DENDRITIC CELL NEOPLASM (BPDCN) INTO SUBTYPES

(71) Applicant: JAPANESE FOUNDATION FOR CANCER RESEARCH, Tokyo (JP)

(72) Inventors: Kengo Takeuchi, Tokyo (JP); Kana Sakamoto, Tokyo (JP); Ryohei Katayama, Tokyo (JP); Seiji Sakata, Tokyo (JP)

(73) Assignee: JAPANESE FOUNDATION FOR CANCER RESEARCH, Tokyo (JP)

( * ) Notice: Subject to any disclaimer, the term of this patent is extended or adjusted under 35 U.S.C. 154(b) by 0 days.

(21) Appl. No.: 18/314,267

(22) Filed: May 9, 2023

(65) Prior Publication Data

US 2023/0323475 A1     Oct. 12, 2023

Related U.S. Application Data

(62) Division of application No. 16/076,886, filed as application No. PCT/JP2017/004298 on Feb. 7, 2017, now abandoned.

(30) Foreign Application Priority Data

Feb. 9, 2016     (JP) ................................. 2016-023141

(51) Int. Cl.
| | |
|---|---|
| *C12Q 1/6886* | (2018.01) |
| *A61K 31/167* | (2006.01) |
| *A61K 31/4045* | (2006.01) |
| *A61K 31/4745* | (2006.01) |
| *A61K 31/55* | (2006.01) |
| *A61K 31/551* | (2006.01) |
| *A61K 31/635* | (2006.01) |
| *A61K 31/675* | (2006.01) |
| *A61K 45/00* | (2006.01) |
| *A61P 35/02* | (2006.01) |
| *A61P 43/00* | (2006.01) |
| *G01N 33/50* | (2006.01) |
| *G01N 33/575* | (2026.01) |
| *G01N 33/57505* | (2026.01) |

(52) U.S. Cl.
CPC .......... *C12Q 1/6886* (2013.01); *A61K 31/167* (2013.01); *A61K 31/4045* (2013.01); *A61K 31/4745* (2013.01); *A61K 31/55* (2013.01); *A61K 31/551* (2013.01); *A61K 31/635* (2013.01); *A61K 31/675* (2013.01); *A61K 45/00* (2013.01); *A61P 35/02* (2018.01); *A61P 43/00* (2018.01); *G01N 33/5011* (2013.01); *G01N 33/5023* (2013.01); *G01N 33/5047* (2013.01); *G01N 33/57505* (2026.01); *G01N 33/57575* (2026.01); *C12Q 2600/158* (2013.01); *G01N 2333/82* (2013.01); *G01N 2800/56* (2013.01)

(58) Field of Classification Search
CPC ............ C12Q 1/6886; C12Q 2600/158; G01N 33/48; G01N 33/5011; G01N 33/5023; G01N 33/57505; A61P 35/02
See application file for complete search history.

(56) References Cited

U.S. PATENT DOCUMENTS

| | | |
|---|---|---|
| 2003/0129626 A1 | 7/2003 | Nielsen et al. |
| 2013/0171638 A1 | 7/2013 | Zhang et al. |
| 2016/0096892 A1 | 4/2016 | Brogdon et al. |

FOREIGN PATENT DOCUMENTS

| | | |
|---|---|---|
| JP | 2002-527077 | 8/2002 |
| JP | 2005-524384 A | 8/2005 |
| JP | 2007-44008 | 2/2007 |
| JP | 2015-503348 A | 2/2015 |
| WO | 2014/187856 A1 | 11/2014 |
| WO | 2015/026892 | 2/2015 |
| WO | 2015/144636 | 10/2015 |
| WO | 2016/014576 | 1/2016 |

OTHER PUBLICATIONS

Fu (Cancer Genetics, 2013, V 206, pp. 293-298).*
Chaidos (Ther Adv Hematol, 2015, vol. 6(3): 128-141).*
Juppner (Bone, 11995, vol. 17, p. 39S-42S).*
Dermer, G.B. (Bio/Technology (1994) 12: 320).*
Jain et al, J Natl Compr Canc Netw 2023, 21(5):515-521.*
Wang (Medicine, 2023, 102:7, pp. 1-8).*
Cazzato (Hematology Reports, 2023, vol. 15, 676-706).*
Chen (Leukemia & Lymphoma, 2021, vol. 62, pp. 528-537).*
Adachi, et al. "High Expression of CD56 (N-CAM) in a Patient with Cutaneous CD4-Positive Lymphoma"; American Journal of Hematology, 1994, vol. 47, p. 278-282, 5 pages.

(Continued)

*Primary Examiner* — Sarae L Bausch
(74) *Attorney, Agent, or Firm* — Rankin, Hill & Clark LLP

(57)     ABSTRACT

The diagnostic markers that provide novel diagnostic criteria to blastic plasmacytoid dendritic cell neoplasm (BPDCN) has been searched, and the presence of immunoblastoid cytomorphology, 8q24 rearrangement, and MYC expression were established as novel markers for subtyping BPDCN. It has been further found that the inhibitors which directly or indirectly inhibit the expression, functions, or signaling pathways of MYC, such as BET bromodomain-selective inhibitors or aurora kinase inhibitors, are effective in MYC-positive BPDCN, and HDAC inhibitors or BCL2 family protein inhibitors are effective as therapeutic drugs for BPDCN.

4 Claims, 9 Drawing Sheets

(56)            References Cited

OTHER PUBLICATIONS

Benet, et al., "Histologic and Immunohistologic Characterization of Skin Localization of Myeloid Disorders", Am. J. Clin. Pathol; 2011, vol. 135, p. 278-290, 13 pages.

Cronin, et al., "Immunophenotypic Analysis of Myeloperoxidase-Negative Leukemia Cutis and Blastic Plasmacytoid Dendritic Cell Neoplasm", Am. J. Clin. Pathol., 2012, vol. 37, p. 367-376, 10 pages.

Sangle, et al., "Optimized Immunohistochemical Panel to Differentiate Myeloid Sarcoma from Blastic Plasmacytoid Dendritic Cell Neoplasm", Modern Pathology, 2014, vol. 27, p. 1137-1143, 7 pages.

Petrella, et al., "Tumoral Aspects of Plasmacytoid Dendritic Cells: What do we know in 2009?", 2010, Autoimmunity, vol. 43, p. 210-214, 6 pages.

Knowles, et al. "Knowles' Neoplastic Hematopathology", Chapter 42, Plasmacytoid Dendritic Cell Neoplasm, 2014, p. 1058-1075, Wolters Kluwer, Lippincott Williams & Wilkins, 9 pages.

Riaz, et al., "Blastic Plasmacytoid Dendritic Cell Neoplasm: Update on Molecular Biology, Diagnosis, and Therapy", Cancer Control, 2014, vol. 21, No. 4, p. 279-289, 11 pages.

Julia, et al., "Blastic Plasmacytoid Dendritic Cell Neoplasms", May 2014, Am. J. Surg. Pathol. vol. 38, No. 5, p. 673-680, 8 pages.

Marafioti, et al., "Novel Markers of Normal and Neoplastic Human Plasmacytoid Dendritic Cells", 2008, Blood, vol. 111, p. 3778-3792, 16 pages.

Pulford, et al., "The BCL 11Axl Transcription Factor: Its Distribution in Normal and Malignant Tissues and Use as a Marker for Plasmacytoid Dendritic Cells", Leukemia, 2006, vol. 20, p. 1439-1441, 3 pages.

Maeda, et al., "A Novel Plasmacytoid Dendritic Cell Line, CAL-1, Established from a Patient with Blastic Natural Killer Cell Lymphoma", International Journal of Hematology, Mar. 2005, vol. 81 (2), p. 148-154, 8 pages.

Narita, et al., "A Leukemic Plasmacytoid Dendritic Cell Line, PMDC05, with the Ability to Secrete IFN-α by Stimulation via Toll-like Receptors and Present Antigens to Naive T Cells", Leukemia Research, vol. 33 (9), p. 1224-1232, 9 pages.

Yang, et al., "Therapeutic Potential of a Synthetic Lethal Interaction between the MYC Proto-Oncogene and Inhibition of Aurora-B Kinase", 2010, Proc. Natl. Acad. Sci. USA, vol. 107 (31), p. 13836-13841, 6 pages.

Dauch, et al., "A MYC-Aurora Kinase A Protein Complex Represents an Actionable Drug Target in p53-Altered Liver Cancer", 2016, Nature Medicine vol. 22 (7), p. 744-753, 12 pages.

International Preliminary Report on Patentabiliy, PCT/JP2017/004298, dated Aug. 14, 2018, 8 pages.

International Search Report, PCT/JP2017/004298, dated May 9, 2017, 5 pages.

Kawamoto, et al. "t (6;8) (p21;q24) o Tomonatta Blastic Plasmacytoid Dendritic Cell Neoplasm (BPDCN) no ichirei", The Journal of the Japanese Society of Lymphoreticular Tissue, Jun. 6, 2014, vol. 54, p. 115, 3 pages.

Extended European Search Report dated Aug. 21, 2019, Application No. 17 750 223.4, 11 pages.

Y Nakamura et al., "Identification of SUPT3H as a novel 8q24/MYC partner in blastic plasmacytoid dendritic cell neoplasm with t(6;8)(p21;q24) translocation", Blood Cancer Journal (2015), vol. 5, 3 pages.

Maro Ohanian et al., "Acute myeloid leukemia with MYC rearrangement and JAK2 V617F mutation", Cancer Genetics, (2015), vol. 208, No. 11, pp. 571-574, Elsevier Inc.

Hisao Nagoshi et al., "Frequent PVT1 Rearrangement and Novel Chimeric Genes PVT1-NBEA and PVT1-WWOX Occur in Multiple Myeloma with 8q24 Abnormality", Cancer Research (2012), vol. 72, No. 19, pp. 4954-4962.

Steven I. Park et al., "Paper: Alisertib, an Aurora a Kinase Inhibitor, Induces Synthetic Lethality and Overcomes Chemoresistance in Myc-Overexpressing Lymphoma Cells", ASH 57th Annual Meeting & Exposition, Dec. 5, 2015, 2 pages, Orlando, FL.

Kana Sakamoto et al., "Recurrent 8q24 rearrangement in blastic plasmacytoid dendritic cell neoplasm: association with immunoblastoid cytomorphology, MYC expression, and drug response", Leukemia (2018), vol. 32 No. 12, pp. 2950-2603, Nature Publishing Group UK, London.

European Office Action dated Nov. 20, 2020, Application No. 17 750 223.4, 7 pages.

Japanese Office Action dated Apr. 4, 2022, Application No. 2017-566940; English machine translation included, 6 pages.

Clone RP11-47304, GenBank AC022973.5 (submitted 2000, printed Feb. 2021 available at ncbi.nlm.nih.gov, pp. 1-51).

Alignment for AC022973.5 and KF495742.1 (Genome Reference Consortium, ncbi.nlm.nih.gov, printed Feb. 2021, pp. 1-23).

* cited by examiner

Figure 1 (A)  Immunoblastoid cytomorphology
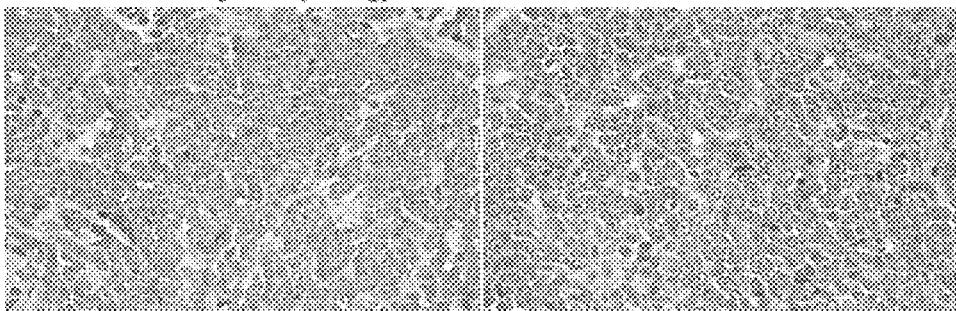
Figure 1 (B)  Classical cytomorphology
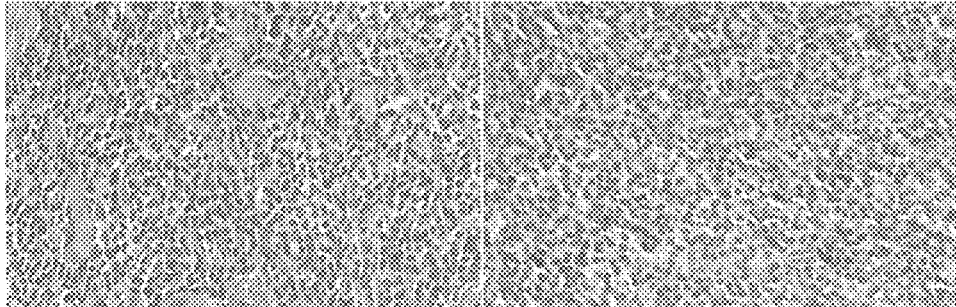
Figure 1 (C)  Classical cytomorphology
(variants)
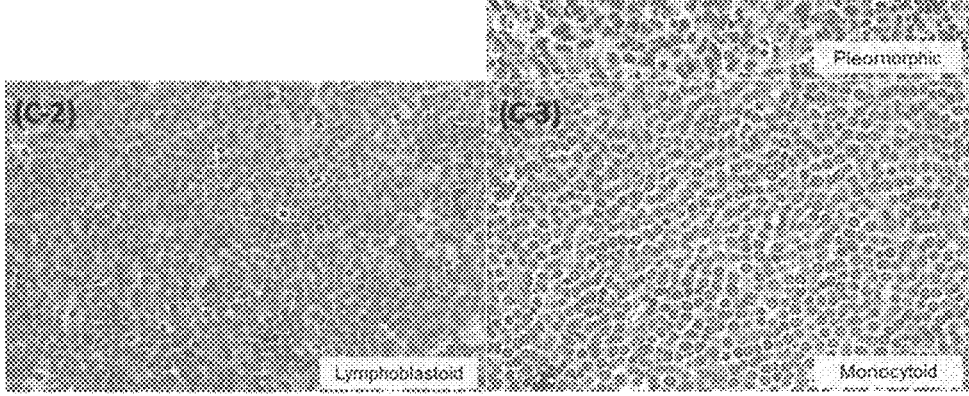

Figure 3
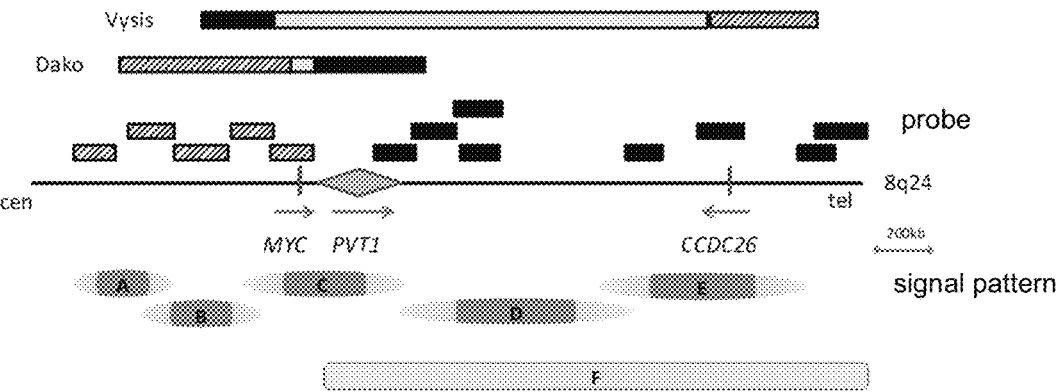
Figure 4
MYC+ group
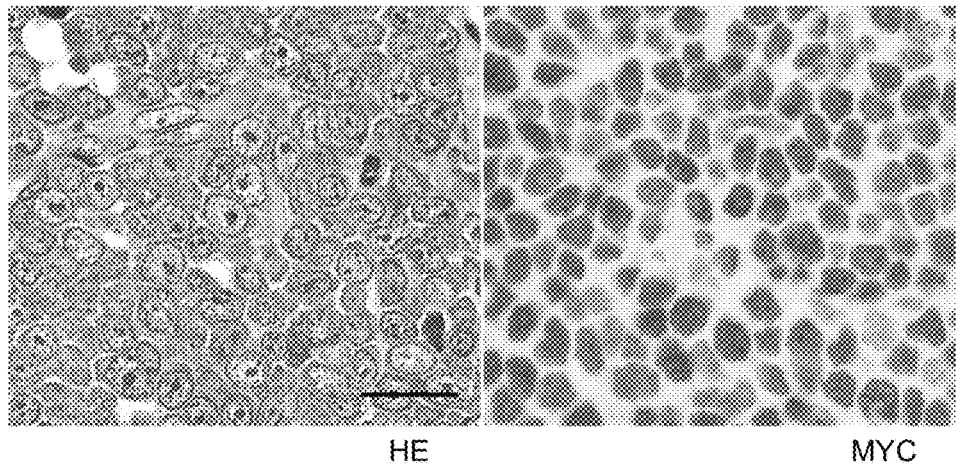
MYC- group
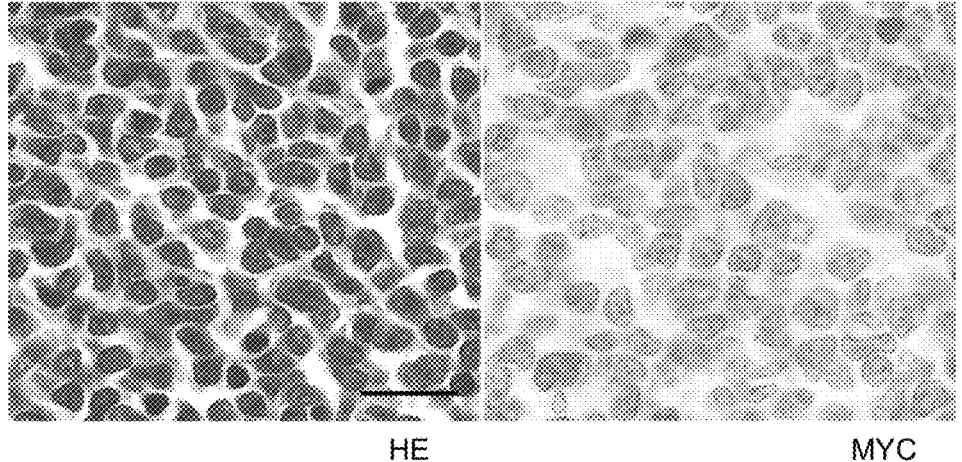

Figure 5
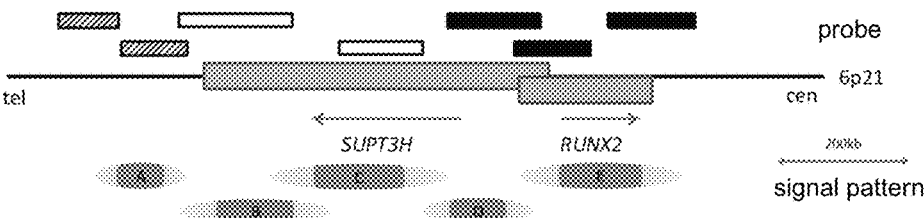
Figure 6
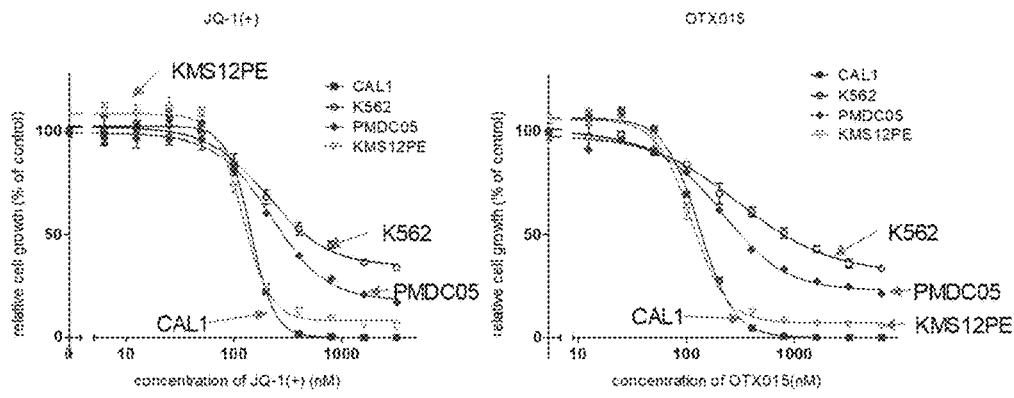
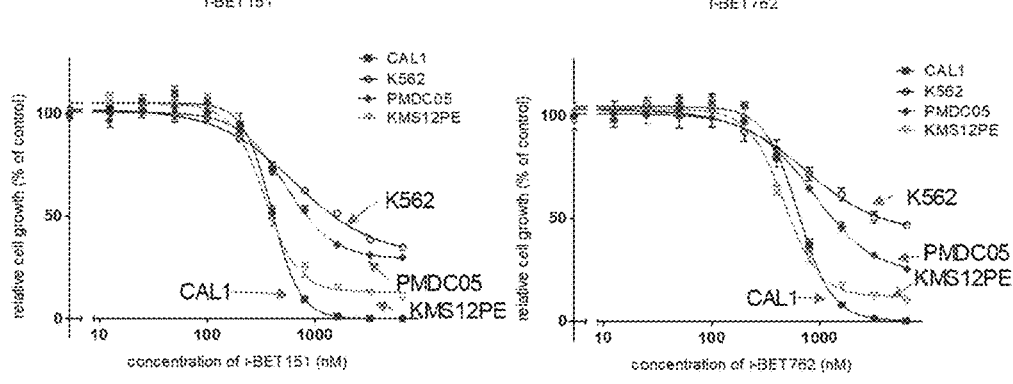
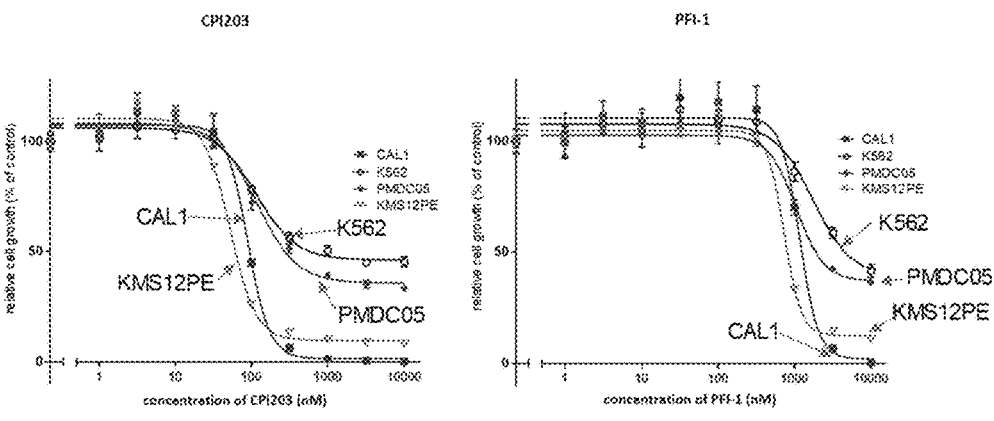

| Markers | MYC+ | % | MYC- | % | P value |
|---|---|---|---|---|---|
| CD4 | 37/38 | 97 | 56/59 | 95 | 1 |
| CD56 | 32/38 | 84 | 58/59 | 98 | 0.014 |
| CD123 | 37/38 | 97 | 58/58 | 100 | 0.4 |
| BDCA2 | 35/36 | 97 | 58/59 | 98 | 1 |
| TCL1 | 38/38 | 100 | 58/59 | 98 | 1 |
| CD2AP | 7/7 | 100 | 9/10 | 90 | 1 |
| BCL11a | 7/7 | 100 | 9/9 | 100 | - |
| CD1a | 0/7 | 0 | 0/9 | 0 | - |
| CD2 | 4/23 | 17 | 11/39 | 28 | 0.38 |
| CD3 | 0/37 | 0 | 0/58 | 0 | - |
| CD5 | 0/32 | 0 | 3/40 | 7.5 | 0.25 |
| CD7 | 21/25 | 84 | 26/40 | 65 | 0.15 |
| CD8 | 0/33 | 0 | 0/45 | 0 | - |
| CD10 | 10/29 | 34 | 2/31 | 6.5 | 0.0093 |
| CD11c | 0/12 | 0 | 0/15 | 0 | - |
| CD13 | 0/12 | 0 | 3/21 | 14 | 0.28 |
| CD14 | 1/10 | 10 | 0/12 | 0 | 0.46 |
| CD15 | 0/3 | 0 | 2/7 | 29 | 1 |
| CD16 | 0/20 | 0 | 0/24 | 0 | - |
| CD19 | 0/21 | 0 | 0/30 | 0 | - |
| CD20 | 0/35 | 0 | 0/52 | 0 | - |
| CD21 | 0/7 | 0 | 0/1 | 0 | - |
| CD22 | 0/2 | 0 | 0/7 | 0 | - |
| CD23 | 0/12 | 0 | 1/11 | 9 | 0.48 |
| CD24 | 0/1 | 0 | 0/2 | 0 | - |
| CD25 | 0/14 | 0 | 1/22 | 5 | 1 |
| CD30 | 0/31 | 0 | 0/34 | 0 | - |
| CD33 | 11/15 | 73 | 11/25 | 44 | 0.1 |
| CD34 | 0/32 | 0 | 0/42 | 0 | - |
| CD38 | 2/5 | 40 | 11/12 | 92 | 0.055 |
| CD41 | 0/4 | 0 | 0/4 | 0 | - |
| CD43 | 6/8 | 75 | 8/8 | 100 | 0.47 |
| LCA | 18/19 | 95 | 17/17 | 100 | 1 |
| CD45RO | 0/14 | 0 | 1/15 | 7 | 1 |
| CD57 | 0/8 | 0 | 0/8 | 0 | - |
| CD68 | 2/26 | 7.7 | 11/42 | 26 | 0.11 |
| CD79a | 4/24 | 17 | 2/28 | 7.1 | 0.4 |
| CD99 | 3/5 | 60 | 3/6 | 50 | 1 |
| CD117 (c-kit) | 1/12 | 8.3 | 0/5 | 0 | 1 |
| CD138 | 0/8 | 0 | 0/5 | 0 | - |
| Myeloperoxidase | 0/31 | 0 | 0/40 | 0 | - |
| Lysozyme | 0/8 | 0 | 0/7 | 0 | - |
| HLA-DR | 11/11 | 100 | 26/26 | 100 | - |
| Granzyme B | 0/18 | 0 | 0/19 | 0 | - |
| TIA-1 | 0/17 | 0 | 0/22 | 0 | - |
| perforin | 0/3 | 0 | 0/5 | 0 | - |
| EBV | 0/24 | 0 | 0/36 | 0 | - |
| MUM1 | 1/5 | 20 | 1/2 | 50 | 1 |
| BCL2 | 7/7 | 100 | 11/11 | 100 | - |
| BCL6 | 0/3 | 0 | 1/4 | 25 | 1 |
| S100 | 0/9 | 0 | 1/11 | 9.1 | 1 |

Figure 13

| No. | Cytomorphology | MYC classifica tion | 8q24 abnormal ity | 8q24 partner | SUPT3H split FISH |
|---|---|---|---|---|---|
| 2 | Immunoblastoid | | + | 8q34 | WT |
| 4 | Immunoblastoid | | - | | WT |
| 5 | Immunoblastoid | | + | 6p12 | split |
| 6 | Immunoblastoid | | - | | WT |
| 7 | Immunoblastoid | | - | | split |
| 11 | Immunoblastoid | | - | | WT (amp) |
| 15 | Immunoblastoid | | + | 6p21 | split |
| 16 | Immunoblastoid | | + | 22q11.2 | WT |
| 20 | Immunoblastoid | | + | unknown | split |
| 21 | Immunoblastoid | MYC+ | - | | WT |
| 22 | Immunoblastoid | | - | unknown | WT |
| 23 | Immunoblastoid | | + | 6p21 | split |
| 26 | Immunoblastoid | | - | | WT |
| 27 | Immunoblastoid | | + | 6p21 | split |
| 28 | Immunoblastoid | | + | 6p21 | split |
| 30 | Immunoblastoid | | + | 8q34 | WT |
| 32 | Immunoblastoid | | + | 6p21 | split |
| 33 | Immunoblastoid | | - | | |
| 34 | Immunoblastoid | | + | 6p21 | split |
| 38 | Immunoblastoid | | + | unknown | WT |
| 42 | Intermediate | | - | | WT |
| 43 | Classical | MYCa | - | | |
| 44 | Intermediate | | + | 8q34 | WT |
| 45 | Intermediate | | - | | WT |
| 48 | Intermediate | | - | | |
| 49 | Intermediate | | - | | WT |
| 50 | Intermediate | | - | | WT |
| 54 | Classical | | - | | |
| 55 | Classical | | - | | WT (amp) |
| 60 | Classical | | - | | WT |
| 61 | Classical | | - | | WT |
| 62 | Classical | | - | | |
| 63 | Classical | | - | | WT |
| 66 | Classical | | + | 18q21, 14q32 | |
| 67 | Classical | | - | | WT |
| 70 | Classical | | - | | |
| 76 | Classical | | - | | WT |
| 78 | Classical | | - | | WT |
| 79 | Classical | | - | | |
| 80 | Classical | MYC- | - | | WT |
| 82 | Classical | | - | | |
| 84 | Classical | | - | | |
| 86 | Classical | | - | | WT |
| 88 | Classical | | - | | WT |
| 89 | Classical | | - | | WT |
| 90 | Classical | | - | | |
| 94 | Classical | | + | unknown | WT |
| 95 | Classical | | - | | WT |
| 98 | Classical | | - | | |
| 99 | Classical | | - | | |
| 100 | Classical | | - | | WT (amp) |
| 101 | Classical | | - | | WT (amp) |
| 102 | Classical | | - | | WT |
| 106 | Classical | | - | | WT |
| 107 | Classical | | - | | |
| 110 | Classical | NE | + | 12p11.2 | |
| 113 | Immunoblastoid | | - | | |

TEST METHOD OF DIVIDING BLASTIC PLASMACYTOID DENDRITIC CELL NEOPLASM (BPDCN) INTO SUBTYPES

CROSS-REFERENCE TO RELATED APPLICATIONS

This application is a divisional of U.S. patent application Ser. No. 16/076,886, filed Sep. 24, 2018, which is the U.S. National Phase under 35 U.S.C. 371 of International Application No. PCT/JP2017/004298, filed on Feb. 7, 2017 which, in turn, claims the benefit of the priority of JP application No. 2016-023141 and having a filing date of Feb. 9, 2016. All of the applications referred to in this paragraph are hereby incorporated herein by reference.

TECHNICAL FIELD

The present invention relates to diagnostic markers of blastic plasmacytoid dendritic cell neoplasm (BPDCN) which is a rare hematopoietic neoplasm, and a method for screening for a novel therapeutic drug.

BACKGROUND ART

Blastic plasmacytoid dendritic cell neoplasm (hereinafter, referred to as BPDCN) is a rare hematopoietic neoplasm reportedly derived from undifferentiated plasmacytoid dendritic cells (pDC). Typically, this neoplasm develops skin lesions and is an aggressive disease with poor prognosis and a median survival period about of 12 months. BPDCN often responds to chemotherapy at the beginning but recurs early, resulting in leukemic change.

BPDCN was reported as skin lymphoma positive for CD4 and CD56 and negative for T cell markers in 1994 by Adachi et al. (Non Patent Literature 1). Since then, also because of being a rare disease, its name had been changed many times due to change in disease concepts until the name of BPDCN appeared as an independent disease entity included in acute myeloid leukemia (AML)-related neoplasms in WHO Classification, the fourth edition, in 2008.

Although BPDCN is now recognized as an independent disease entity, no defined diagnostic criterion has been established. Along with the rarity of the disease, BPDCN is difficult to be distinguished from other hematopoietic neoplasms in practice. Particularly, distinguishing BPDCN from the skin infiltration of AML is most difficult because of its cytomorphology, immunophenotype, and clinical conditions (Non Patent Literatures 2 to 4). CD4, CD56, CD123, TCL1, BDCA2, CD2AP, BCL11A, and others are known as characteristic markers of BPDCN. However, some cases with BPDCN are negative for some of these markers, whereas cases with other diseases such as AML are often positive for these markers (Non Patent Literatures 5 to 8). Therefore, in previous researches and case reports on BPDCN, evaluation of the immunophenotype and diagnostic criteria are highly variable.

As mentioned above, BPDCN is a disease with poor prognosis and is managed without defined standard treatment. Various treatment methods such as ALL (acute lymphocytic leukemia) regimen, AML (acute myeloid leukemia) regimen, or radiotherapy alone are used at present. The understanding of the pathogenesis and the development of an effective treatment method of BPDCN have been demanded.

CITATION LIST

Non Patent Literature

Non Patent Literature 1: Adachi, M. et al., 1994, Am. J. Hematol., Vol. 47, p. 278-282.

Non Patent Literature 2: Benet, C. et al., 2011, Am. J. Clin. Pathol., Vol. 135, p. 278-290.

Non Patent Literature 3: Cronin, D. M. et al., 2012, Am. J. Clin. Pathol., Vol. 37, p. 367-376.

Non Patent Literature 4: Sangle, N. A. et al., 2014, Mod. Pathol., Vol. 27, p. 1137-1143.

Non Patent Literature 5: Petrella, T. et al., 2010, Autoimmunity, Vol. 43, p. 210-214.

Non Patent Literature 6: Knowles, D. M. et al., 2014, "Knowles' neoplastic hematopathology", Wolters Kluwer, Lippincott Williams & Wilkins.

Non Patent Literature 7: Riaz, W. et al., 2014, Cancer Control, Vol. 21, p. 279-289.

Non Patent Literature 8: Julia, F. et al., 2014, Am. J. Surg. Pathol., Vol. 38, p. 673-680.

Non Patent Literature 9: Marafioti, T. et al., 2008, Blood, Vol. 111, p. 3778-3792.

Non Patent Literature 10: Pulford, K. et al., 2006, Leukemia, Vol. 20, p. 1439-1441.

Non Patent Literature 11: Maeda, T. et al., 2005, Int. J. Hematol. Vol. 81 (2), p. 148-54.

Non Patent Literature 12: Narita, M. et al., 2009, Leuk Res. Vol. 33 (9), p. 1224-32.

Non Patent Literature 13: Yang, D. et al., 2010, Proc. Natl. Acad. Sci. USA, Vol. 107 (31), p. 13836-13841.

Non Patent Literature 14: Dauch, D. et al., 2016, Nat. Med., Vol. 22 (7), p. 744-753.

SUMMARY OF INVENTION

Technical Problem

An object of the present invention is to search for a novel diagnostic marker of BPDCN for which diagnostic criteria have not yet been defined. A further object of the present invention is to establish clear diagnostic criteria by the diagnostic marker and to provide a novel therapeutic drug and a method for screening for a therapeutic drug.

Solution to Problem

The present invention relates to a novel diagnostic marker of BPDCN, a test method based on the diagnostic marker, a therapeutic drug, and a method for screening for a therapeutic drug.

(1) A test method comprising dividing blastic plasmacytoid dendritic cell neoplasm (BPDCN) into subtypes by testing at least any one of immunoblastoid morphology, 8q24 rearrangement, and MYC expression in BPDCN.

(2) A diagnostic marker for dividing BPDCN into the subtypes, comprising at least any one of immunoblastoid morphological marker, 8q24 rearrangement, and MYC expression in BPDCN.

(3) A pharmaceutical composition for treating BPDCN, comprising a substance that directly or indirectly inhibits MYC expression, MYC functions, or signaling pathways involving MYC, as an active ingredient.

(4) The pharmaceutical composition according to (3), wherein the BPDCN to be treated is a case to be treated which is positive for at least any one marker selected from immunoblastoid cytomorphology, 8q24 rearrangement, and MYC expression.

(5) The pharmaceutical composition according to (3) or (4), wherein the active ingredient is a BET (bromodomain and extra terminal) bromodomain-selective inhibitor or an aurora kinase inhibitor.

(6) The pharmaceutical composition according to (5), wherein the BET bromodomain-selective inhibitor is JQ1, I-BET151, I-BET762, OTX015, CPI203, PFI-1 or an analog compound thereof, and the aurora kinase inhibitor is alisertib, barasertib or an analog compound thereof.

(7) A pharmaceutical composition for treating BPDCN, comprising a HDAC inhibitor or a BCL2 family protein inhibitor as an active ingredient.

(8) The pharmaceutical composition, whereinthe HDAC inhibitor is vorinostat, panobinostat or an analog compound thereof, and the BCL2 family protein inhibitor is venetoclax or an analog compound thereof.

(9) A probe set for detecting the diagnostic marker according to (2), wherein the diagnostic marker is 8q24 rearrangement, and the probe is a FISH probe set which detects 8q24 rearrangement by comprising a telomeric probe which comprises a sequence of at least consecutive 20 bp in the sequence of CTD-2527N12 and is capable of specifically hybridizing to CTD-2527N12, and a probe which comprises a sequence of at least consecutive 20 bp of a centromeric region positioned upstream of MYC gene and is capable of specifically hybridizing to the centromeric region.

(10) A method for screening for a therapeutic drug for BPDCN, comprising adding a candidate compound to medium of a BPDCN cell line, and using change in MYC expression and/or cell growth by the candidate compound as an index.

(11) The method for screening for a therapeutic drug for BPDCN according to (10), wherein the BPDCN cell line is CAL-1 cell line and/or PMDC05 cell line.

(12) A method for screening for a therapeutic drug for BPDCN, comprising using change in MYC expression by a candidate compound as an index.

Advantageous Effects of Invention

The present invention has enabled to provide a novel therapeutic drug by newly identifying diagnostic markers to subdivide BPDCN. Also, the present invention can be applied to the screening of a novel therapeutic drug.

BRIEF DESCRIPTION OF DRAWINGS

FIG. 1 is a staining image showing the typical cytomorphology of BPDCN. FIG. 1(A) shows a staining image of an immunoblastoid group, FIG. 1(B) shows a staining image of a classical group, and FIG. 1(C) shows a staining image of variants of the classical group.

FIG. 3 is a diagram showing the design of MYC split FISH probes and MYC split FISH signal patterns in cases of MYC+ and MYCa groups.

FIG. 4 is a diagram showing MYC immunostaining.

FIG. 5 is a diagram showing the design of SUPT3H split FISH probes and SUPT3H split FISH signal patterns in cases of MYC+ and MYCa groups.

FIG. 6 is a diagram showing the growth suppression of various neoplastic cell lines by BET bromodomain-selective inhibitors.

FIG. 12 depicts a table which summarizes the results of comparing immunohistochemical markers between the MYC$^+$BPDCN and the MYC$^-$BPDCN.

FIG. 13 depicts a table which summarizes the results of chromosome analysis (G-banding).

DESCRIPTION OF EMBODIMENTS

Figure 2:
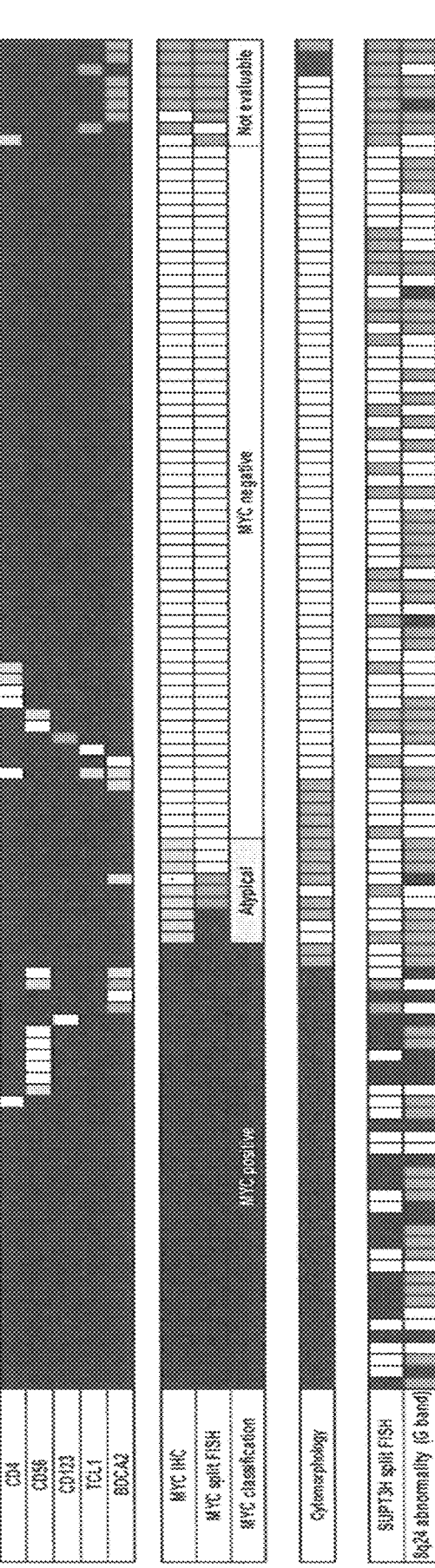
FIG. 2 is a diagram showing the immunophenotype and gene rearrangement of BPDCN.

The present inventors have conducted detailed molecular pathological studies on BPDCN and consequently found markers that can divide BPDCN into at least two subtypes. The present inventors have revealed that neoplasms currently diagnosed as BPDCN can be divided into two subtypes on the basis of 8q24 rearrangement, MYC expression, and cytomorphology, though the details will be described below.

8q24 rearrangement, one of the markers for subtyping of BPDCN, may be detected by use of any method such as G-banding or split FISH as long as the method can detect the rearrangement of the region.

Increased expression of MYC may be detected by use of any method as long as the method is capable of detecting the MYC expression at the protein level or the RNA level. The method for analysis at the protein level includes immunostaining, Western blot, and the like. The method for analysis at the RNA level includes RT-PCR, quantitative RT-PCR, cDNA microarray method, RNA sequencing using a next-generation sequencer, and the like. Any of the methods may be used. Particularly, analysis by immunostaining is preferred because tissues are obtained in a limited amount and because cytomorphology can also be analyzed in parallel.

The present inventors have found that not only can BPDCN be divided into subtypes by use of the markers of the present invention, but an agent suppressing MYC expression reduces cell growth as to a MYC-positive group (a group positive in MYC immunostaining and positive in MYC split FISH is defined as a MYC-positive group and also referred to as a MYC$^+$BPDCN, though the details will be described below). Thus, the MYC$^+$BPDCN of BPDCN may be treated by the administration of an agent suppressing MYC expression.

Such a MYC expression inhibitor may be any agent as long as the agent can suppress the function of MYC. Specifically, an agent that can directly or indirectly suppress MYC expression, or an agent that inhibits the downstream signaling system of MYC may be used as a therapeutic drug for BPDCN. Alternatively, an agent that functionally inhibits MYC may be used. Examples of the inhibitor decreasing MYC expression include 10058-F4, curcumin, asarinin, CHC004, CHC005, CHC008, CHC011, and BET (bromodomain and extra terminal) bromodomain-selective inhibitors disclosed in the present invention. Also, examples of the agent that inhibits the MYC signaling pathway include STAT3 inhibitors and Wnt/β-catenin inhibitors.

These known agents suppressing MYC expression or function can be used as therapeutic drugs for BPDCN. Particularly, a BET bromodomain-selective inhibitor shown herein to have a remarkable suppressive effect can be effectively used. Examples of the BET bromodomain-selective inhibitor include JQ1, I-BET151, I-BET762, OTX015, CPI203, and PFI-1 whose effects will be shown below as well as RVX-208, GSK2801, and bromosporine. Other BET bromodomain-selective inhibitors serving as pharmaceutical compounds that can suppress MYC expression can also be used, as a matter of course.

Aurora kinase inhibitors considered to control the function of MYC can also be used as therapeutic drugs for BPDCN. An aurora A kinase-selective inhibitor, alisertib, and an aurora B kinase-selective inhibitor, barasertib, were both found effective for the growth suppression of BPDCN cell lines that exhibited MYC expression. Hence, the aurora kinase inhibitors may be used in the treatment of BPDCN.

The method for screening for a novel compound according to the present invention can be performed by adding a candidate compound to a medium of a BPDCN cell line highly expressing MYC, such as CAL-1, or a MYC expression-negative cell line such as PMDC05. After the addition of the candidate compound, a compound can be selected by using the survival rate of the cells as an index for screening. When using the cell lines highly expressing MYC a compound can be selected by the decreased expression of MYC as an index. In the case of using MYC expression as an index, the cells used do not have to be a BPDCN-derived cell line and can be cells having an increased expression of MYC. For example, a plasma cell neoplasm KMS12PE cell line that exhibits an increased expression of MYC may be used. Further, a BPDCN-derived cell line can be used for screening a therapeutic drug with cell growth suppression as an index, regardless of MYC expression. In addition to CAL-1 and PMDC05, GEN2.2 and the like are known as cells established from BPDCN. Cell lines that will be established in the future can be used, as a matter of course.

Since the BET bromodomain-selective inhibitors and the aurora kinase inhibitors were effective, the screening can be efficiently performed by using, as a candidate compound, a compound having an inhibitory effect on BET family protein, an aurora kinase inhibitor, or a compound known to decrease MYC expression. HDAC inhibitors and BCL2 family protein inhibitors were compounds having a cell growth suppressive effect on BPDCN cell lines, regardless of the presence or absence of MYC expression. Thus, these inhibitors are also likely to act as therapeutic drugs for BPDCN.

Hereinafter, the present invention will be specifically described.

1. Subject

Cases were collected and analyzed with the approval of the ethical review committee of the Japanese Foundation For Cancer Research. We have collected cases diagnosed with BPDCN or the previous diagnostic name, blastic NK-cell lymphoma. Unstained slides from cases diagnosed with BPDCN at each institution, frozen specimens preserved at each institution, and clinical information were collected from the institutions in Japan who had published papers on BPDCN in English or Japanese and other cooperative institutions. Finally, 153 cases were collected from 56 facilities.

The diagnosis of BPDCN was reexamined as to the collected cases. On the basis of the report of Julia et al., eligibility was determined under a condition of positivity to 4 or more markers among 5 markers: CD4, CD56, CD123, TCL1, and BDCA2 (Non Patent Literature 8). This criterion is considered as a criterion for confirming the diagnosis of BPDCN at the strictest level at this moment.

Immunostaining results at the Japanese Foundation for Cancer Research or at the facilities providing the specimens were used. In atypical cases and cases that were difficult to be distinguished from AML, the immunostaining of lysozyme, myeloperoxidase (MPO), and the like were performed as appropriate. The clinical information was collected from electronic medical records for the cases of our institution and questionnaires and presented papers for the cases of other facilities. Lesions that appeared before the start of initial treatment were regarded as primary lesions. For untreated cases, lesions that appeared before definite diagnosis were regarded as primary lesions. The characteristics of skin lesions were classified into 3 types: tumors, patches/plaques, and mixed character (tumor and patches/plaques mixed). The distributions of skin lesions were classified into generalized (lesions were present at two or more areas in the body) and localized (solitary lesions, or lesions present within one area, such as the chest, of the body) distributions.

Among the 153 cases diagnosed with BPDCN or a relative disease at the 56 facilities, 116 cases satisfied the eligibility criteria of this study (positivity to 4 or more markers among 5 markers: CD4, CD56, CD123, TCL1, and BDCA2; hereinafter, referred to as 4/5 marker positivity) and received definite diagnosis of BPDCN. Thirty-seven cases did not satisfy the eligibility criteria of this study and were thus confirmed diagnosis as not BPDCN, though diagnosed with BPDCN at the facilities providing the specimens (these cases are referred to as an "other" group). As a result of reevaluating the cytomorphology of the 4/5 marker-positive cases, AML was suspected in one case because of irregularly shaped nuclei with cleavage in the neoplastic cells. This case was positive for CD4, CD56, and CD123, negative for TCL1, and focally positive for BDCA2, but strongly positive for lysozyme, and was therefore included in the other group. As a result, 115 cases of BPDCN and 38 cases of the "other" group were obtained.

The biopsied sites in the 38 cases that did not satisfy the diagnostic criteria of BPDCN and were thus determined as the other group were the skin (21 specimens), the bone marrow (10 specimens), lymph node (9 specimens), and others (6 specimens). From histological findings, marker findings, clinical courses, etc., presumptive diagnosis was made: 23 cases with AML that exhibited a tendency to differentiate into the myelomonocytic lineage, or myeloid sarcoma, 2 cases with immature hematopoietic neoplasm of unknown lineage, 2 cases with T cell lymphoma, 1 case with embryonal rhabdomyosarcoma, and 10 unclassified cases.

The primary lesions in the cases that received definite diagnosis of BPDCN from 4/5 marker positivity were most commonly the skin for 106 cases (95%), and only 6 cases had no skin lesion. Bone marrow lesions were observed in 60 cases (63%) while peripheral blood infiltration was observed in 38 cases (38%). Concurrent or preceding myelodysplasia was observed in 13 (20%) out of 65 cases on which data was obtained. The most common characteristics of skin lesions were tumors for 53 cases (55%). The distributions of skin lesions were generalized for 49 cases (49%) and localized for 50 cases (51%), which were almost the same number.

2. Cytomorphology

First, results of analysis of cytomorphology in 115 cases with determined BPDCN is shown. The cytomorphology was evaluated by HE staining. As shown in FIG. 1, a didactically classical group that had fine chromatin, a medium-size irregular nucleus, and a small to medium amount of cytoplasm and exhibited no nucleoli or one or more small nucleoli (hereinafter, referred to as a classical group; FIG. 1(B)), and totally unlike it, a group of cases that principally had immunoblastoid cells which resembled immunoblasts, which had a round to ovoid vacuolated nucleus, a medium amount of basophilic cytoplasm, and a large bright central nucleolus but had fine chromatin (hereinafter, referred to as the immunoblastoid group; FIG. 1(A)) were observed.

Cases having less than 20% of large cells with a conspicuous central nucleolus like immunoblastoid cells, were included in the classical group. The classical group varied and included cytomorphological variants that may be called pleomorphic (FIG. 1(C-1)), lymphoblastoid (FIG. 1(C-2)), and monocytoid (FIG. 1(C-3)).

The conventional cytomorphology of BPDCN is reportedly the morphology of the classical group mentioned above. Sixty-three out of the 115 cases analyzed corresponded to this classical group. However, the immunoblastoid group which exhibited characteristic morphology with a round to ovoid nucleus and one central nucleolus was found in 38 cases, which were approximately 30% of the whole. None of the previous reports systemically summarized the presence of immunoblastoid cytomorphology as shown in FIG. 1(A) in BPDCN.

3. Immunostaining

Next, results of immunostaining are shown. A formalin-fixed paraffin embedded specimen was sliced into 4 μm thick and immunostained with antibodies against CD4, CD56, CD123, TCL1, and BDCA2 used in the diagnostic criteria for BPDCN as well as antibodies against MYC, CD2AP, Bcl11A, lysozyme, and myeloperoxidase. Evaluation was conducted mainly with the number of positive neoplastic cells, and the intensity of the staining was not taken into consideration.

The following antibodies were used: CD4: clone 4B12, manufactured by Nichirei Corp., CD56: clone 1B6, manufactured by Leica Biosystems Nussloch GmbH, CD123: clone 7G3, manufactured by BD Biosciences, TCL1: clone EPR3949, manufactured by Abcam plc, BDCA2: clone 124B3.13, manufactured by Dendritics SAS, MYC: clone Y69, manufactured by Abcam plc, CD2AP: clone B-4, manufactured by Santa Cruz Biotechnology, Inc., Bcl11A: rabbit polyclonal antibody manufactured by Atlas Antibodies, lysozyme: rabbit polyclonal antibody manufactured by Nichirei Corp., myeloperoxidase: rabbit polyclonal antibody manufactured by Dako/Agilent Technologies, Inc.

FIG. 2 shows the results of staining of the 5 markers used in the diagnostic criteria. Each column depicts each patient and is indicated by black for positive and by white for negative in all the staining results. Also, light gray represents partially positive, and dark gray represents that evaluation was unable.

Among the cases studied for the 5 markers CD4, CD56, CD123, BDCA2, and TCL1 used in the diagnostic criteria for BPDCN, 89 cases were positive for the 5 markers, and 15 cases were positive for 4 markers. Among the cases studied for 4 markers, 11 cases were positive for the 4 markers. CD4 was positive in 111 cases (97%), CD56 was positive in 108 cases (94%), CD123 was positive in 113 cases (99%), BDCA2 was positive in 105 cases (98%), and TCL1 was positive in 112 cases (99%). The number of the negative cases was 4, 7, 1, 2, and 1, respectively.

MYC immunostaining (FIG. 2, MYC IHC) was determined as positive when 70% or more neoplastic cells were stained, as heterogeneous when 20% or more and less than 70% neoplastic cells were stained, and as negative when less than 20% neoplastic cells were stained. As a result, the number of positive cases (indicated by black in FIG. 2) was 38, that of negative cases (indicated by white in FIG. 2) was 62, and 8 cases were found heterogeneous (indicated by light gray in FIG. 2). Seven cases were found unevaluable (indicated by dark gray in FIG. 2).

4. Analysis by Split FISH

An unstained section of a formalin-fixed paraffin-embedded specimen sliced into 4 μm thick was analyzed by FISH. DNA probes prepared from bacterial artificial chromosome (BAC) clones were used. Hybridized slides were counterstained with 4',6-diamidino-2-phenylindole (DAPI) and observed under a fluorescence microscope, BX51 (Olympus Corp.). Samples were regarded as being positive when split signals were observed in 70% or more of neoplastic cells, as being heterogeneous when split signals were observed in 10% or more and less than 70% of neoplastic cells, and as being negative when split signals were observed in less than 10% of neoplastic cells. The probes were designed by focusing on MYC having a gene locus on 8q24 and SUPT3H having a gene locus on 6p21. SUPT3H is a gene reported as a partner of 8q24 rearrangement in a case. The BAC clones used are as described below.

MYC (green): RP11-153B5, RP11-739G15, CTD-2530E12, CTD-2313L9, CTD-3066D1

MYC (red): CTD-2369J14, RP11-161B19, RP11-195G18, RP11-69H6, CTD-2384G12, RP11-420E20, CTD-3089D15, CTD-2527N12 SUPT3H (green): RP11-342H9, RP4-669F6

SUPT3H (blue): RP11-315C4, CTC-328A8

SUPT3H (red): RP11-213118, RP1-244F24, CTD-2515K5

Five regions marked with oblique lines in FIG. 3 depict the positions of the MYC (green) probes used in the present invention. Eight regions indicated by black depict the positions of the MYC (red) probes on the 8q24 chromosome. The approximate positions of FISH probes obtained from Abbott Laboratories Inc. (Vysis) and Dako/Agilent Technologies, Inc. (Dako) are shown in the upper region of FIG. 3. Regions A, B, C, D, and E depict the areas of breakpoints on the genome, and region F depicts a region of deletion on the genome.

Signal patterns of MYC split FISH varied among cases, some of which exhibited a breakpoint in regions A, B, C, D, or E and some of which exhibited deletion in region F. Although cases considered to have breakpoints on 8q24 within the PVT1 gene (pattern C) were most common (17 cases), a putative breakpoint on 8q24 differed among the cases and was observed both upstream and downstream of the MYC gene locus.

At present, FISH probes for MYC are commercially available from two companies, Abbott Laboratories Inc. and Dako/Agilent Technologies, Inc. However, as shown in FIG. 3, the BPDCN cases involved rearrangement that cannot be detected at least by the probe from Dako/Agilent Technologies, Inc. For using 8q24 rearrangement as a diagnostic marker that contributes to BPDCN subtyping, it is necessary to use a probe that covers a wide region. Specifically, for detecting the 8q24 chromosome rearrangement in BPDCN, it is necessary to use CTD-2527N12 (sequence information, etc. are available from www.ncbi.nlm.nih.gov/clone/57254/) serving as the most telomeric probe used in this study. For such a probe, it is not necessary to use the whole sequence of CTD-2527N12, and nucleic acid which include a sequence at least consecutive 20 bp of CTD-2527N12 and specifically hybridizes to CTD-2527N12 is enough.

Any probe may be used as a centromeric probe as long as the probe is positioned in a region upstream of the MYC gene. An arbitrary sequence which contains consecutive 20 bp within a region of any of the 5 probes used in this study, RP11-153B5 (sequence information is available from www.ncbi.nlm.nih.gov/clone/221383/), RP11-739G15 (sequence information is available from www.ncbi.nlm.nih-.gov/clone/283769), CTD-2530E12 is available from (sequence information www.ncbi.nlm.nih.gov/clone/58094/), CTD-2313L9 information is (sequence available from www.ncbi.nlm.nih.gov/clone/25175/), and CTD-3066D1 (sequence information is available from www.ncbi.nlm.nih-.gov/clone/129332/), may be used as such a probe, or a region positioned more centromeric may be used as the probe.

MYC split FISH was positive in 41 cases, MYC split FISH was negative in 63 cases, and MYC split FISH was heterogeneous in 3 cases (see FIG. 2, MYC split FISH).

5. Correlation Between MYC Classification and Cytomorphology

For MYC classification, a case positive in MYC immunostaining and positive in MYC split FISH was subclassified into the MYC-positive (MYC+) group, and a case negative in MYC immunostaining and negative in MYC split FISH was subclassified into the MYC-negative (MYC−) group. Cases corresponding to neither of these groups were included in the MYC atypical (MYCa) group.

Nine out of the 115 cases were unable to evaluate for MYC status due to a shortage of residual specimens. Among the 106 cases evaluable, 38 cases (36%) were subclassified into the MYC+BPDCN, 59 cases (56%) were subclassified into the MYC−BPDCN, and 9 cases (8%) were subclassified into the MYCa group (see FIG. 2, MYC classification).

Cytomorphological classification and MYC classification are summarized in Table 1. In the immunoblastoid group, all the cases except for the 2 cases unable to evaluate for MYC status were subclassified into the MYC+BPDCN (36/36, 100%). On the other hand, in the classical group, all the cases except for 3 MYCa cases were subclassified into the MYC−BPDCN (54/57, 95%). Thus, the presence or absence of abnormalities in MYC correlated strongly with the cytomorphology (P<0.0001). As for 14 cases in the intermediate group of cytomorphology, 2 cases were MYC+, 5 cases were MYC−, 6 cases were MYCa, and 1 case was unable to evaluate for MYC status. FIG. 4 shows the typical HE staining images and MYC immunostaining images of the cases of the MYC+ (immunoblastoid) and the MYC− (classical) groups.

TABLE 1

| | MYC+ | MYC− | MYCa | Total | Pvalue |
|---|---|---|---|---|---|
| Immunoblastoid | 36 | 0 | 0 | 36 | <0.0001 |
| Classical | 0 | 54 | 3 | 57 | |
| Intermediate | 2 | 5 | 6 | 13 | |
| Total | 38 | 59 | 9 | 106 | |

As shown in Table 1 and FIG. 2, among the specimens classified into the immunoblastoid group by HE staining, all the 36 cases evaluable for the MYC status were subclassified into the MYC+BPDCN. On the other hand, the 57 cases classified into the classical group by HE staining were subclassified into the MYC−BPDCN except for 3 cases.

The details of the 9 cases classified into the MYCa group is shown. Cases positive in MYC split FISH but heterogeneous in MYC immunostaining were 3 cases, 2 out of which exhibited classical cytomorphology and 1 out of which exhibited intermediate cytomorphology. Cases heterogeneous in both MYC split FISH analysis and MYC immunostaining were 3 cases, 2 out of which exhibited intermediate cytomorphology and 1 out of which exhibited atypical cytomorphology. 3 cases were negative in MYC split FISH and positive for 20 to 30% neoplastic cells in MYC immunostaining, and exhibited intermediate cytomorphology.

Taken together, the analysis results described above demonstrated that the immunoblastoid cytomorphology, increased expression of MYC, and 8q24 chromosome rearrangement are strongly associated in BPDCN (see FIG. 2).

6. Comparative Study Between MYC+BPDCN and MYC−BPDCN

As a result of comparing patients' background, such as age, sex, initial treatment (chemotherapy, radiotherapy), involved lesions, characteristics and distributions of skin lesions, and peripheral blood findings, between the MYC+BPDCN and the MYC−BPDCN, significant difference was observed in age, the presence or absence of liver lesions, hemoglobin level, characteristics of skin lesions, and the rate of undergoing hematopoietic stem cell transplantation (Table 2). The median age of the MYC+BPDCN was 71 years old (37 to 83 years old), and that of the MYC−BPDCN was 64 years old (3 to 88 years old). Thus, the median age was significantly higher in the MYC+BPDCN (P=0.022). Five pediatric cases below the age of 18 years were included in the MYC−BPDCN, whereas no such cases were found in the MYC+BPDCN. These results demonstrated that patients' ages also differed between the MYC+BPDCN and the MYC−BPDCN.

In comparing prognosis between the MYC+BPDCN and the MYC−BPDCN, significant difference was not observed in survival time but was observed in remission rate ascribable to initial treatment. Clinical course was unknown in some cases involved in this study. Among the 115 cases classified as BPDCN, the initial treatment was known in 97 cases, and therapeutic effects were known in 85 cases. The survival time was known in 98 cases with a median survival of 366 days and a 2-year survival rate of 53.3%. Sixty-nine cases (81%) exhibited at least partial response (PR) by initial treatment, and 50 cases (59%) exhibited complete response (CR). Thirty-eight out of the cases that exhibited at least PR underwent recurrence (38/65, 58%), and 32 cases for which the number of days from diagnosis to recurrence was known had a median value of 203 days (77 to 3650 days). Cases that underwent hematopoietic stem cell transplantation had a significantly longer survival time (P<0.0001), suggesting that long-term survival can be expected for cases capable of receiving transplantation.

When a survival time was compared between the MYC+BPDCN and the MYC−BPDCN, no significant difference was observed. However, the number of the cases with data whether or not achieved CR were 30 cases in the MYC+BPDCN and 38 cases in the MYC−BPDCN, and CR was achieved in 14 cases (47%) and 28 cases (74%) in the MYC+ and MYC−BPDCNs, respectively. Thus, the CR rate was significantly higher in the MYC−BPDCN compared with the MYC+BPDCN (P=0.027). The PR rate was 20 out of 30 cases (66%) for the MYC+BPDCN and 37 out of 42 cases (88%) for the MYC−BPDCN and was thus also significantly higher in the MYC−BPDCN (P=0.039).

TABLE 2

| Factor | | Group | MYC+ | % | MYC− | % | P value |
|---|---|---|---|---|---|---|---|
| | Age | median (range) | 71 (37-83) | — | 64 (3-88) | — | 0.022 |
| | | Adult/Children | 38/0 | Adult: 100 | 53/5 | Adult: 91 | 0.15 |
| | Sex | Male/Female | 35/3 | M:F = 12:1 | 49/10 | M:F =4.9:1 | 0.24 |
| | Prior Chemotherapy or radiotherapy | | 4/28 | 14 | 4/35 | 11 | 1 |
| | Preceeding or coexistent myeloid abnormality | | 3/27 | 11 | 8/32 | 25 | 0.2 |
| Lesion | Skin | | 37/38 | 97 | 52/56 | 93 | 0.65 |
| | Bone marrow (at diagnosis) | | 19/32 | 59 | 36/50 | 72 | 0.34 |
| | Bone marrow blasts (%) (median*) | | 73 | — | 47 | — | 0.23 |
| | Bone marrow (throughout the course) | | 25/31 | 81 | 39/46 | 85 | 0.76 |
| | Peripheral blood | | 15/35 | 43 | 19/52 | 37 | 0.66 |
| | Lymph nodes | | 23/35 | 66 | 29/49 | 59 | 0.65 |
| | Spleen | | 5/34 | 15 | 15/47 | 32 | 0.12 |
| | Liver | | 0/33 | 0 | 6/47 | 13 | 0.039 |
| | Nasopharynx | | 1/32 | 3.1 | 7/47 | 15 | 0.13 |
| | Other | | 1/32 | 3.1 | 4/47 | 8.5 | 0.64 |
| Skin lesions | Gross appearance | mixed | 4 | 11 | 16 | 35 | 0.0017 |
| | | patch or plaque | 3 | 8 | 11 | 24 | |
| | | tumor | 29 | 81 | 19 | 41 | |
| | Distribution | generalized | 8 | 22 | 30 | 65 | 0.00013 |
| | | localized | 29 | 78 | 16 | 35 | |
| | Body site | generalized | 8 | 22 | 30 | 65 | — |
| | | trunk | 15 | 42 | 9 | 19 | |
| | | head | 8 | 22 | 3 | 6 | |
| | | upper limb | 4 | 11 | 2 | 4 | |
| | | lower limb | 1 | 3 | 3 | 6 | |
| Peripheral blood count | WBC (/μl) | median (range) | 6600 (2140-174000) | — | 4950 (500-36450) | — | 0.065 |
| | Blasts (%) | median* (range) | 21 (0.5-95) | — | 20.6 (1.0-76) | — | 0.91 |
| | Monocytes (%) | median (range) | 6.5 (0-20) | — | 7 (0-24.5) | — | 0.24 |
| | Hemoglobin (g/dl) | median (range) | 13.5 (10.2-15.7) | — | 12.2 (4.7-16.3) | — | 0.041 |
| | Platelet (x10^4/μl) | median (range) | 13.5 (0.2-29.4) | — | 11.7 (2.8-41.5) | — | 0.62 |
| | LDH(IU/I) | median (range) | 286 (140-10738) | — | 260 (134-2103) | — | 0.11 |
| | LDH elevation | | 17/34 | 50 | 20/44 | 45 | 0.82 |
| | B symptioms | | 1/33 | 3 | 5/40 | 13 | 0.21 |
| | SUVmax | median (range) | 3.4 (1.4-15.5) | — | 4.6 (1.6-10.8) | — | 0.57 |
| | Cytogenotic abnormalities | | 17/20 | 89 | 11/30 | 37 | 0.0012 |
| Treatment | appearance of symptoms to commencement of therapy (months) | median (range) | 3.8 (0.25-13) | — | 4.5 (0.03-18) | — | 0.44 |
| | First line treatment | ALL-like | 5 | 15 | 13 | 28 | 0.4 |
| | | AML-like | 3 | 9 | 1 | 2 | |
| | | lymphoma-like | 20 | 59 | 23 | 49 | |
| | | radiotherapy | 2 | 6 | 5 | 11 | |
| | | none/paliative | 4 | 12 | 5 | 11 | |
| | Stem cell transplantation | Yes | 3/34 | 8.8 | 15/46 | 33 | 0.015 |
| | | Allogeneic | 1 | | 14** | | 0.056 |
| | | Autologous | 2 | | 1 | | |

There was no significant difference in lesion sites except for the liver. None of the 33 cases in the MYC⁺BPDCN manifested liver lesions, whereas 6 out of the 47 cases in the MYC⁻BPDCN manifested liver lesions. The hemoglobin level was 13.5 g/dl as a median value (10 to 15.7 g/dl) for the MYC⁺BPDCN, whereas it tended to be lower in the MYC⁻BPDCN with a median value of 12.2 g/dl (4.7 to 16.3 g/dl). No significant difference was observed in the other peripheral blood findings.

The characteristics and distributions of skin lesions differed between the MYC⁺BPDCN and the MYC⁻BPDCN. As for the characteristics of skin lesions, tumors were observed in as many as 29 cases (81%) of the MYC⁺ BPDCN, whereas more than half of the cases in the MYC⁻ BPDCN manifested patches/plaques or mixed lesions (P=0.0017). The distributions of skin lesions also differed between the groups. Localized lesions were observed in as many as 29 cases (78%) of the MYC⁺BPDCN, whereas generalized lesions were observed in as many as 30 cases (65%) in the MYC⁻BPDCN (P=0.0001). Cases that received hematopoietic stem cell transplantation were 3 cases (8.8%) in the MYC⁺BPDCN vs. 15 cases (33%) in the MYC⁻ BPDCN and were thus a significantly more in the MYC⁻ BPDCN (P=0.015).

Some cases in the immunoblastoid group and the intermediate group having unusual cytomorphology were also evaluated for CD2AP (Non Patent Literature 9) and BCL11A (Non Patent Literature 10) known as markers with high specificity for BPDCN in order to confirm the diagnosis of BPDCN. All the cases tested were positive for both the 2 markers (confirmed for 7 cases in the immunoblastoid group and 4 cases in the intermediate group). In addition, no case was found positive for the lineage markers, such as CD3, CD20, myeloperoxidase (MPO), and lysozyme.

As a result of comparing immunohistochemical markers between the MYC⁺BPDCN and the MYC⁻BPDCN, 58 out of 59 cases (98%) in the MYC⁻BPDCN were positive for CD56, whereas the positive rate in the MYC⁺BPDCN remained at 32 out of 38 cases (84%), showing significant difference (P=0.014). Also, 10 out of 29 cases (34%) in the MYC⁺BPDCN were positive for CD10, whereas only 2 out of 31 cases (6%) in the MYC⁻BPDCN were positive thereto (P=0.0093). The detailed results are summarized in the table shown in FIG. 12.

7. Structural Chromosome Abnormality

Next, the results of chromosome analysis (G-banding) were summarized. The results of chromosome analysis were obtained in 57 cases. Some abnormality was detected for a total of 31 cases (54%) with 17 out of 20 cases (85%) in the MYC⁺BPDCN, 11 out of 30 cases (37%) in the MYC⁻BPDCN, 1 out of 4 MYCa cases (25%), and 2 out of 3 cases unable to evaluate for MYC status. The chromosome analysis results about the 57 cases are shown in the table shown in FIG. 13. The G-banding was performed by a routine method.

The ratio of cases having a detected chromosome abnormality significantly differed between the MYC⁺BPDCN and the MYC⁻BPDCN (P=0.0012). The detected chromosome abnormalities were summarized as follows: additional material on 12p11.1 was most commonly detected for 7 cases (7/57, 12%), followed by deletion of chromosome 13, deletion of chromosome 9, deletion of chromosome 15, and t(6;8)(p21; q24) (or additional material on 6p21 and 8q24) for 6 cases each (6/57, 11%). In the MYC⁺BPDCN, abnormalities involving the MYC gene locus 8q24, were detected in 12 cases among 19 cases with obtained results. As a result of focusing on the chromosome with which rearrangement with 8q24 occurred in these 12 cases, t(6;8)(p21; q24) or additional materials on both was most commonly seen (6 cases). Two cases had t(8;9)(q24; q34), and t(6;8)(p12; q24) and t(8;22)(q24; q11.2) was observed in 1 case each.

As breakpoints of 8q24 were not constant as mentioned above, breakpoints of its most frequent fusion partner, 6p21, were also not constant. Results of SUPTH split FISH analysis are shown in FIG. 5. In FIG. 5, 2 regions indicated by oblique line depict the positions of the SUPTH (green) probes used in the present invention. Two regions indicated by white depict the positions of the SUPTH (blue) probes. Three regions indicated by black depict the positions of the SUPTH (red) probes. Regions of A, B, C, D, and E depict the regions of breakpoints on the genome.

By analyzing 36 cases in the MYC⁺BPDCN with SUPT3H split FISH, 6 cases found to have t(6;8)(p21; q24) in chromosome analysis, 1 case found to have t(6;8)(p12; q24), 10 cases without chromosome analysis results, and 2 cases with unknown rearrangement partner were positive for SUPT3H split. Accordingly, a total of 19 cases showed positive results (19/36, 53%). In the MYC⁻BPDCN, chromosome abnormalities involving 8q24 were observed in 3 cases, all of which were however negative in MYC split FISH, suggesting that these abnormalities were not associated with the MYC gene. One MYCa case was found to have additional material on 8q24 in 16/20 cells, which also had additional material on 9q34.

8. Effect of Agents Suppressing MYC Expression

Since BPDCN was broadly classified on the basis of MYC expression, the growth of the cells of the MYC⁺BPDCN (the immunoblastoid group of cytomorphology) of BPDCN may be suppressed by the suppression of MYC expression. Accordingly, analysis was conducted using cultured BPDCN cells highly expressing MYC.

The cell lines used were 4 lines: BPDCN cell lines CAL-1 (MYC⁺BPDCN; Non Patent Literature 11; obtained from Nagasaki University) and PMDC05 (MYC⁻BPDCN; Non Patent Literature 12; obtained from Niigata University), a positive control plasma cell neoplasm KMS12PE (obtained from JCRB Cell Bank) having the increased expression of MYC, and a negative control leukemia cell line K562 (obtained from JCRB Cell Bank) in which no MYC gene rearrangement was seen.

The CAL-1, PMDC05, or KMN12PE cells at 4000 cells/well or K562 at 1000 cells/well were inoculated to 96-well cell culture plates. The survival rates of these cells were analyzed 48 hours after addition of the BET bromodomain-selective inhibitors, JQ1 (manufactured by Abcam plc), I-BET151 (manufactured by ChemieTek), I-BET762 (manufactured by ChemieTek), or OTX015 (manufactured by Selleck Chemicals LLC) from 6.25 nM to 6400 nM, or CPI203 (manufactured by Cayman Chemical Company) or PFI-1 (manufactured by Cayman Chemical Company) from 1 nm to 10000 nM, to the RPMI medium supplemented with GlutaMAX (manufactured by Thermo Fisher Scientific Inc.) and 10% FBS. The cell survival rates were measured using a cell growth assay kit using CTG reagent (Cell Titer-Glo, manufactured by Promega Corp.).

As shown in FIG. 6, the survival rate of the BPDCN cell line, CAL-1 belonging to the MYC⁺BPDCN was rapidly decreased by the addition of JQ1 when the concentration exceeded 150 nM. By contrast, PMDC05 belonging to the MYC⁻BPDCN exhibited a high survival rate, as in the negative control K562, even when JQ1 was added at a high concentration of 1000 nM or more. In the case of using I-BET151, I-BET762, OTX015, CPI203, or PFI-1, the survival rate of the CAL-1 cell line was also sharply decreased with the addition of these compounds serving as BET bromodomain-selective inhibitors. On the other hand, PMDC05 exhibited a high survival rate even when I-BET151, I-BET762, OTX015, CPI203, or PFI-1 was added at a high concentration.

Figure 7:
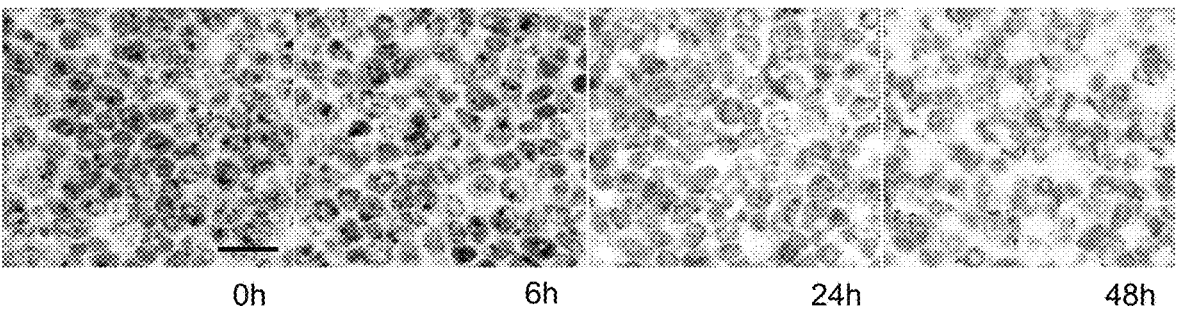
FIG. 7 is an immunostaining image showing MYC expression after BET bromodomain-selective inhibitor treatment.

In order to confirm that the addition of the BET bromodomain-selective inhibitor decreased MYC expression, 400 nM JQ1 was added to CAL-1 cells, which were then analyzed for the degree of MYC expression over time by immunostaining. As shown in FIG. 7, time-dependent decrease in MYC expression was observed. The ratios of MYC-positive cells at the time of JQ1 addition (0 hours), 6 hours later, 24 hours later, and 48 hours later were approximately 95%, 60%, 15%, and 0%, respectively. Good correlation was observed between decrease in cell survival rate and decrease in MYC expression level.

Next, MYC expression after BET bromodomain-selective inhibitor addition was analyzed by Western blot using BPDCN cell lines, CAL-1 belonging to the MYC⁺BPDCN and PMDC05 belonging to the MYC⁻BPDCN.

The MYC expression levels in the cells cultured for 2 hours after addition of each of the BET bromodomain-selective inhibitors, JQ1 (400 nM), I-BET151 (1000 nM), I-BET762 (2000 nM), and OTX015 (1000 nM), were confirmed by Western blot.

Figure 8:
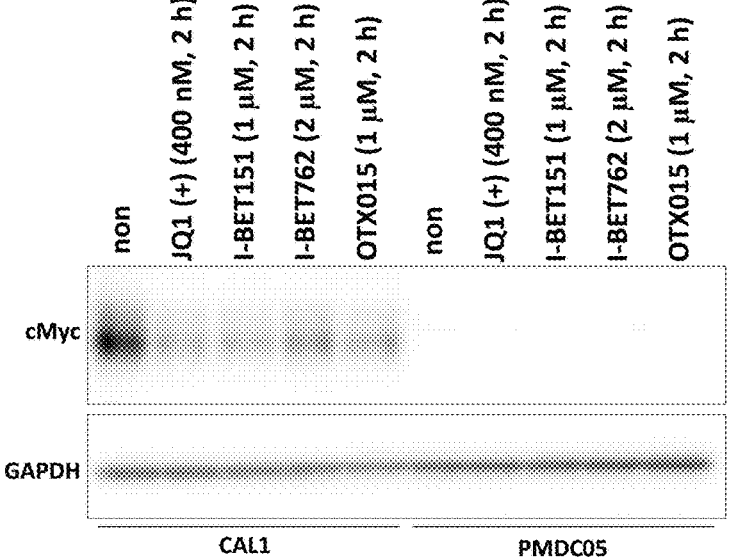
FIG. 8 is a Western blotting image showing MYC expression after BET bromodomain-selective inhibitor treatment.

The primary antibody used was anti-cMyc rabbit monoclonal antibody (manufactured by Abcam plc) and an anti-GAPDH mouse monoclonal antibody (manufactured by Merck Millipore) as control. The secondary antibody used was a HRP-labeled anti-rabbit IgG antibody (donkey, manufactured by Amersham Biosciences Corp.). SuperSignal West Femto Maximum Sensitivity Substrate (manufactured by Pierce/Thermo Fisher Scientific Inc.) was used for detection. The results are shown in FIG. 8.

Marked decrease in MYC expression in CAL-1 was confirmed for all of the 4 BET bromodomain-selective inhibitors. In PMDC05 cells, MYC expression was already at an undetectable level without JQ1 treatment.

As mentioned above, it was shown that the cell growth was suppressed by the addition of the BET bromodomain-selective inhibitors to a medium. Next, analysis was conducted on a mechanism underlying the suppression of the cell growth. JQ1 was added to CAL-1, PMDC05, KMS12PE, and K562 cells. Twenty-four hours later, the cells were collected and analyzed by Western blot for MYC expression and PARP cleavage serving as an index for cell death by apoptosis. An anti-PARP antibody was obtained from Cell Signaling Technology, Inc.

Figure 9:
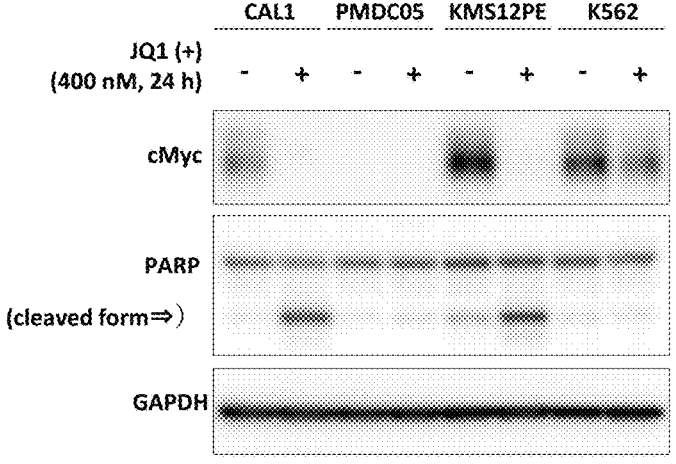
FIG. 9 is a Western blotting image showing MYC expression and apoptosis induction after JQ1 treatment.

As shown in FIG. 9, in the CAL-1 and KMS12PE cells treated with 400 nM of JQ1 for 24 hours, MYC expression was markedly decreased and the expression of cleaved-PARP, an index for cell death by apoptosis, was increased, compared with untreated cells. On the other hand, increased PARP cleavage was not observed in PMDC05 cells or K562 cells, the cells less sensitive to JQ1. These results demonstrated that apoptosis and cell death were induced in the BPDCN cell line, CAL-1, which belongs to the MYC⁺ BPDCN.

As shown above, in the MYC+ BPDCN cells, the BET bromodomain-selective inhibitors decreased the expression of MYC and induced the apoptosis, resulting in decrease in the survival rate of the cells. This indicates the possibility that BPDCN cases of MYC⁺BPDCN, i.e., BPDCN cases that exhibit 8q24 rearrangement, MYC expression, and/or an immunoblastoid morphological marker, can be treated using the BET bromodomain-selective inhibitors. As shown in FIGS. 6 to 9, the cell survival rate was decreased in response to the decreased expression of MYC, suggesting that other agents that can decrease MYC expression, or other agents that inhibits the function or signaling pathway of MYC can also be used.

9. Effects of Other Agents

The increased expression of the aurora kinase is observed in the hematopoietic neoplasms such as leukemia. There is a report showing the synthetic lethality of MYC overexpression and the aurora kinase inhibitors in MYC overexpressed neoplastic cells (Non Patent Literature 13). It has also been shown that the inhibition of the protein interaction between MYC and aurora A kinase by aurora kinase A inhibitors induces the decomposition of MYC and the cell death in hepatocellular carcinoma (Non Patent Literature 14).

Figure 10:
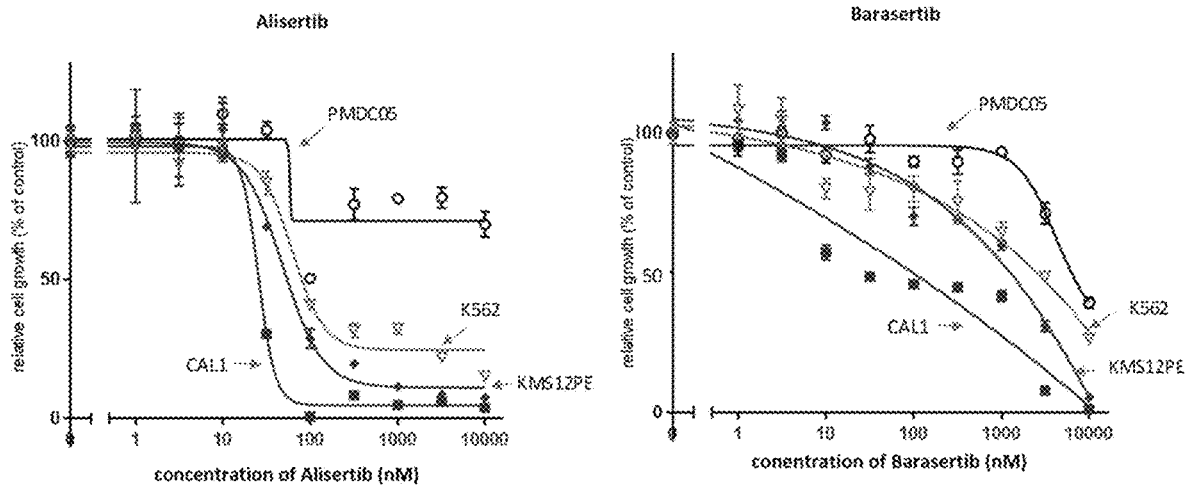
FIG. 10 is a diagram showing the growth suppression of various neoplastic cell lines by aurora kinase inhibitors.

Aurora kinase inhibitors, albeit not agents directly suppressing MYC expression, were analyzed for their effects in the present invention. The effects of an aurora kinase A-selective inhibitor, alisertib (manufactured by Selleck Chemicals LLC), and an aurora kinase B-selective inhibitor, barasertib (manufactured by AdooQ Biosciences LLC), were analyzed in the same way as above using the 4 cell lines: BPDCN cell lines, CAL-1 (MYC⁺BPDCN) and PMDC05 (MYC⁻BPDCN), plasma cell neoplasm, KMS12PE (positive control) having the increased expression of MYC, and a leukemia cell line, K562 (negative control) in which no MYC gene rearrangement was known. Each inhibitor was added from 1 nm to 10000 nM to the medium of the cells of each line. 48 hours later, the survival rates of these cells were analyzed (FIG. 10).

Both alisertib and barasertib exhibited a higher growth suppressive or inhibitory effect on the cells of CAL-1 in which high expression of MYC is observed, compared with the PMDC05 cells. These results suggest that, in the case of using aurora kinase inhibitors in the treatment of BPDCN, MYC expression or 8q24 rearrangement serves as a biomarker for estimating the responsiveness to the aurora kinase inhibitors.

Figure 11:
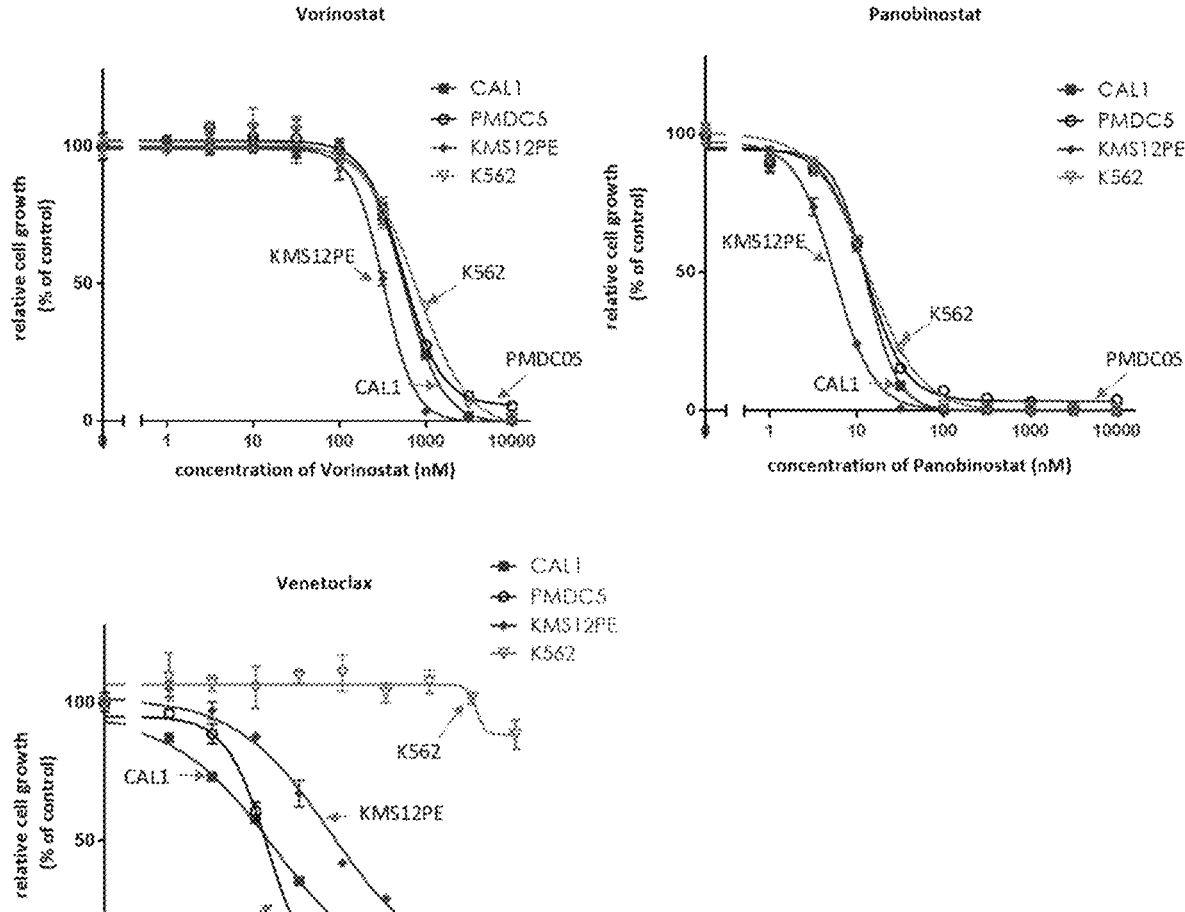
FIG. 11 is a diagram showing the growth suppression of various neoplastic cell lines by HDAC inhibitors and a BCL2 family protein inhibitor.

Agents effective for the growth suppression of BPDCN cell lines were further studied. The study was conducted on HDAC inhibitors, vorinostat (manufactured by Selleck Chemicals LLC) and panobinostat (manufactured by Selleck Chemicals LLC), and a BCL2 family protein inhibitor, venetoclax (manufactured by LKT Laboratories Inc.). Each inhibitor was added in the concentration of 1 nM to 10000 nM to the 4 cell lines described above. The survival rates of these cells were analyzed 48 hours later (FIG. 11). All the inhibitors were found to exhibit a strong inhibitory effect on the BPDCN cell lines, though it was not associated with the presence or absence of MYC expression. These agents have the possibility of serving as a therapeutic drug for BPDCN, for which the treatment options are limited at present.

The present inventors revealed that BPDCN, a disease considered as an independent entity, can be divided into the subtypes on the basis of cytomorphology, 8q24 rearrangement, and/or MYC expression. Because the inhibitors that directly or indirectly inhibit MYC expression can serves as the therapeutic drugs for neoplasms of a MYC-expressing group, to treat cases using the novel biomarkers, such as cytomorphology, in the diagnostic criteria. Furthermore, HDAC inhibitors or BCL2 family protein inhibitors were also found to be effective for BPDCN, regardless of the presence or absence of MYC abnormalities.

The invention claimed is:

1. A method of treatment for a human patient having blastic plasmacytoid dendritic cell neoplasm (BPDCN), the method comprising:
    obtaining a biopsy sample from the patient;
    detecting a 8q24 rearrangement in the sample, the 8q24 rearrangement comprising one of the following: t(6;8) (p21;q24); t(8,9)(q24;q34); t(6,8)(p12;q24); and t(8; 22)(q24;q11.2);
    classifying the BPDCN patient into a BPDCN subtype that has a 8q24 rearrangement; and
    administering a treatment to the patient that has a 8q24 rearrangement, wherein the treatment includes administering one or more bromodomain and extra terminal (BET) bromodomain-selective inhibitors or an aurora kinase inhibitor.

2. The method of claim 1, wherein the detecting is performed by FISH.

3. The method of claim 1, wherein the BET bromodomain-selective inhibitors include one or more of the following: JQ1, I-BET151, I-BET762, OTX015, CP1203, PFI-1, and RVX208.

4. The method of claim 1, wherein detecting is performed by FISH or G-banding.

* * * * *